United States Patent [19]
Cavoy et al.

[11] Patent Number: 6,124,473
[45] Date of Patent: Sep. 26, 2000

[54] PROCESS FOR PREPARING (S)- AND (R)-α-ETHYL-2-OXO-1-PYRROLIDINEACETAMIDE

[75] Inventors: Emile Cavoy, Ham-sur-Heure; Michel Hamende, Uccle; Michel Deleers, Linkebeek; Jean-Pierre Canvat; Vincent Zimmermann, both of Brussels, all of Belgium

[73] Assignee: UCB, S.A., Brussels, Belgium

[21] Appl. No.: 09/306,984

[22] Filed: May 7, 1999

[30] Foreign Application Priority Data

May 8, 1998 [EP] European Pat. Off. .............. 98108429

[51] Int. Cl.$^7$ ................................................ C07D 207/12
[52] U.S. Cl. ............................................................ 548/550
[58] Field of Search ............................................... 548/550

[56] References Cited

U.S. PATENT DOCUMENTS

| | | | |
|---|---|---|---|
| 4,696,942 | 9/1987 | Gobert et al. | 514/424 |
| 4,696,943 | 9/1987 | Gobert et al. | 514/424 |

FOREIGN PATENT DOCUMENTS

| | | |
|---|---|---|
| 0 162 036 | 11/1985 | European Pat. Off. . |
| 0 165 919 | 12/1985 | European Pat. Off. . |
| 0 706 982 | 4/1996 | European Pat. Off. . |

OTHER PUBLICATIONS

Strube et al., Dynamic Simulation of Simulated Moving Bed Chromatographic Processes . . . , Journal of Chromatography, 769, pp. 81–91, Dec. 1997.

J. Strube et al. "Dynamic simulation of simulated moving–bed chromatographic processes for the optimization of chiral separations", Journal of Chromatography A, vol. 769, No. 1, May 2, 1997, pp. 81–92.

E. Cavoy et al., "Laboratory–developed simulated moving bed for chiral drug separations design of the system and separation of tramadol enantiomers", Journal of Chromatography A, vol. 769, No. 1, May 2, 1997, pp. 49–57.

E. Francotte et al., "Applications of simulated moving–bed chromatography to the separation of the enantiomers of chiral drugs", Journal of Chromatography A, vol. 769, May 2, 1997,No. 1, pp. 101–107.

*Primary Examiner*—Joseph McKane
*Assistant Examiner*—Dominic Keating
*Attorney, Agent, or Firm*—Wenderoth, Lind & Ponack, L.L.P.

[57] ABSTRACT

The present invention relates to a process for preparing (S)- and (R)-α-ethyl-2-oxo-1-pyrrolidineacetamide and (R)-α-ethyl-2-oxo-1-pyrrolidineacetamide. According to this process, the enantiomeric resolution of the racemic mixture of α-ethyl-2-oxo-1-pyrrolidineacetamide is carried out by simulated mobile bed chromatography, using at least three columns filled with chiral stationary phase.

This process makes it possible to achieve good production efficiency on the industrial scale.

10 Claims, No Drawings

PROCESS FOR PREPARING (S)- AND (R)-α-ETHYL-2-OXO-1-PYRROLIDINEACETAMIDE

The present invention relates to a novel process for preparing (S)-α-ethyl-2-oxo-1-pyrrolidineacetamide and (R)-α-ethyl-2-oxo-1-pyrrolidineacetamide, corresponding to the formulae

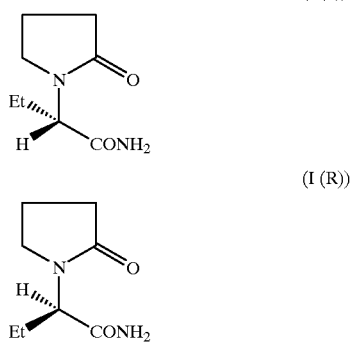

European patent 162,036, in the name of the Applicant, describes (S)-α-ethyl-2-oxo-1-pyrrolidineacetamide, and indicates that it has specific therapeutic properties which distinguish it from the racemic form. By virtue of its properties, the S enantiomer is better suited than the racemic form for the treatment and prevention of attacks of hypoxic and ischaemic type on the central nervous system.

European patent 165,919, also in the name of the Applicant, describes (R)-α-ethyl-2-oxo-1-pyrrolidineacetamide, and indicates that it has specific therapeutic properties which distinguish it from the racemic form. By virtue of its properties, the R enantiomer is better suited for the treatment of cerebral insufficiency, memory disorders, and difficulties both of mental concentration and of learning and studying.

Processes for preparing (S)-α-ethyl-2-oxo-1-pyrrolidineacetamide and (R)-a-ethyl-2-oxo-1-pyrrolidineacetamide are described, respectively, in the abovementioned European patents 162,036 and 165,919. According to these patents, the enantiomers of α-ethyl-2-oxo-1-pyrrolidineacetamide could not be obtained directly from the racemic mixture by resolution. They were thus prepared by other methods and these European patents describe two preparation processes applicable for each respective enantiomer.

In the first manufacturing process, an enantiomer of α-ethyl-2-oxo-1-pyrrolidineacetic acid is reacted successively with an alkyl haloformate, preferably ethyl chloroformate, and ammonia. A certain number of drawbacks are associated with this preparation process during its application on the industrial scale, namely the need to have an optically pure starting product readily available (enantiomer of a-ethyl-2-oxo-1-pyrrolidineacetic acid), as well as certain operating drawbacks such as the formation of an intermediate anhydride which readily decomposes and the difficulty of thermally controlling the operation on a large scale.

In the second process described in European patents 162,036 and 165,919, the enantiomer of an alkyl 4-[[1-(aminocarbonyl)propyl]amino]butyrate or of an N-[1-(aminocarbonyl)propyl]-4-halobutanamide is cyclized, these two compounds themselves being prepared from the enantiomer of the 2-aminobutanamide. The drawback of this process lies in the fact that the enantiomers of the 2-aminobutanamide are not readily available.

Patent GB 2,225,322, also in the name of the Applicant, describes a process for preparing (S)-α-ethyl-2-oxo-1-pyrrolidineacetamide starting with L-methionine. According to this process, the L-methionine is converted into (S)-2-amino-4-(methylthio)butanamide, which is itself converted into (S)-α-[(2-methylthio)ethyl-2-oxo]-1-pyrrolidineacetamide. The latter compound is then subjected to hydrogenolysis using a desulphurization reagent such as Raney nickel in the presence of hydrogen. This method has the advantage of using a widely available optically pure starting material. However, on a large scale, the hydrogenolysis step includes a certain amount of risk, given the presence of hydrogen.

The Applicant set itself the objective of investigating other processes for preparing the enantiomers of α-ethyl-2-oxo-1-pyrrolidineacetamide allowing a technically simpler, less dangerous production which is more efficient on the industrial scale. According to this objective, the Applicant more particularly investigated novel processes for preparing the enantiomers of α-ethyl-2-oxo-1-pyrrolidineacetamide with an optical purity of greater than or equal to 98%, and with good production efficiency on the industrial scale.

The Applicant has just discovered a novel process for preparing the enantiomers of α-ethyl-2-oxo-1-pyrrolidineacetamide, the essential step of which consists in resolving the racemic mixture of α-ethyl-2-oxo-1-pyrrolidineacetamide.

Consequently, the present invention relates to a novel chromatographic process using a chiral stationary phase for preparing (S)-α-ethyl-2-oxo-1-pyrrolidineacetamide and (R)-α-ethyl-2-oxo-1-pyrrolidineacetamide corresponding to the formulae

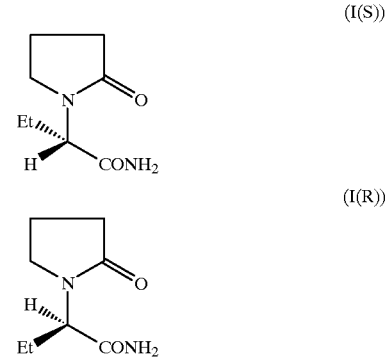

in which the enantiomeric resolution of the racemic mixture of α-ethyl-2-oxo-1-pyrrolidineacetamide is carried out using the simulated mobile bed process, using at least three columns filled with chiral stationary phase.

Given the content of European patents 162,039 and 165,919, there was no reason to hope that the enantiomers of α-ethyl-2-oxo-1-pyrrolidineacetamide could be obtained by a method for the enantiomeric resolution of the corresponding racemic mixture, and certainly not by a chromatographic process.

However, since that time, the technique of simulated mobile bed chromatography has formed the subject of many publications. Mention will be made in particular of U.S. Pat. No. 2,985,589 which describes the operating principle of this technique in detail.

Moreover, European patent 471,082 and European patent application 719,749 describe the use of the simulated mobile bed chromatographic technique for the separation of racemic mixtures. More particularly, these documents describe the resolution of 1,3-butane-diol diacetate and of α-phenylethyl alcohol by means of simulated mobile bed systems comprising 8 or 12 columns filled with chiral stationary phase.

The application of the technique of simulated mobile bed chromatography for the enantiomeric resolution of racemic mixtures has also been described in the article "Lit mobile simulé. Application à la séparation d'isomères optiques [Simulated mobile bed. Application to the separation of optical isomers]" by R. M. Nicoud, Information Chimie No. 368 (May 1995), pp. 113–115. According to this article, the application of the simulated mobile bed technique for the industrial production of optically pure pharmaceutical products is far from being simple: the separations to be carried out are much more difficult and the chromatographic supports are much more expensive than in the case of the existing separations in heavy-tonnage productions; in addition, the simulated mobile bed processes adapted to the requirements of production and of quality in the pharmaceutical industry are extremely sensitive to the operation conditions used, in particular the recycling flow rate and the inlet-outlet flow rate.

There was no reason to hope that the simulated mobile bed technique could be used for the application concerned by the present invention, and above all that this technique could be transposed to the industrial scale to give, efficiently and with excellent production efficiency, a product having the required purity for a pharmaceutical application.

A simulated mobile bed (SML) consists of a series of fixed-bed columns connected in series. The charge (solution to be separated) and the eluent are injected continuously into the system while the purified compounds are removed continuously in the extract (compound most strongly retained) and the raffinate (compound least strongly retained). The points of injection and of removal are shifted in the direction of flow of the mobile phase at constant time intervals, thus simulating a counter-current flow of solid and of liquid. A period is the interval of time which separates two shifts of the points of injection and of removal. A cycle consists of successive periods such that the points of injection and of removal regain their initial positions.

Four zones are defined in a simulated mobile bed, these being delimited by the inlet/outlet points according to:
  zone I: between the eluent and extract points;
  zone II: between the extract and charge points;
  zone III: between the charge and raffinate points;
  zone IV: between the raffinate and eluent points.

Two injection points and two removal points are thus distinguished, which are always arranged between two zones, it being understood that one zone can contain several columns.

In the process according to the invention, a variable number of columns can be used. The simulated mobile bed system must contain a minimum of three columns. In one embodiment of the invention, the simulated mobile bed consists of six columns, of which, in each case, one is in zones I and IV and, in each case, two are in zones II and III. In another embodiment of the invention, two simulated mobile bed systems are used, each containing six columns, these two systems being placed in series, which brings the number of columns used to a total number of twelve. This operating mode makes it possible to carry out the optical resolution of the racemic mixture by passage through the first simulated mobile bed system, and then to further purify the raffinate or the extract by passage through the second simulated mobile bed system. According to this specific embodiment, it may prove to be useful to make use of an intermediate step of concentrating between the passage through the first simulated mobile bed and the passage through the second simulated mobile bed.

It has been noted, surprisingly, that the process according to the present invention makes it possible to obtain, in an industrial plant, (S)-α-ethyl-2-oxo-1-pyrrolidineacetamide with a very high production efficiency, which can be up to 1200 g of (S)-α-ethyl-2-oxo-1-pyrrolidineacetamide per kg of chiral stationary phase and per day and a low volume of consumed and recycled solvent (400 l/kg of (S)-α-ethyl-2-oxo-1-pyrrolidineacetamide produced).

As regards the size of the columns, this can vary within a wide range as a function of the desired production efficiency. Preferably, short columns (from 5 to 50 cm) are used, preferably less than or equal to 10 cm in length.

Different configurations can be used for shifting the injection and removal points. For example, electrostatic or pneumatic valves prove to be suitable for this purpose.

The columns are filled with chiral stationary phase. The chiral stationary phases which can be used according to the present invention can be chosen from phases based on silica gel supporting polymeric compounds such as polysaccharide derivatives (such as esters and carbamates of cellulose or of amylose), polyacrylic derivatives and polyamide derivatives. Examples of phases which can be used according to the invention are the phases Chiralcel (OD, OG, OJ) and Chiralpak (AD, AS) (available from Daicel Chemical Industries), Chirose (C1, etc.) (available from Chiralcep, France), Kromasil (PM 593, etc.) (available from EKA Nobel), Pharmachir (available from A.I.T., France). These chiral stationary phases consist of particles whose size can range between 5 and 300 $\mu$m, preferably from about 10 to 20 $\mu$m.

The eluent which can be used can be varied in natures. Preferably, an alcohol or mixture of alcohol and of alkane in a proportion (by volume) of between 50/50 and 100/0 will be chosen. Ethanol and heptane will preferably be chosen.

According to one preferred embodiment of the process according to the present invention, a recycling pump for ensuring the internal circulation of the fluid is placed between the last and the first column. The presence of this recycling pump not only makes it possible to avoid the risk of pollution of the eluent, but also to minimize the storage problems.

The racemic mixture of α-ethyl-2-oxo-1-pyrrolidineacetamide is obtained by the process described in British patent 1,309,692.

The examples which follow illustrate the process according to the present invention and show operating details with reference to preferred embodiments of the invention, it being clearly understood that the invention is not limited to these specific operating conditions.

EXAMPLE 1

In this example, the enantiomeric resolution of a racemic mixture of α-ethyl-2-oxo-1-pyrrolidineacetamide is carried out in two steps on a Licosep 12-26 system, available from Novasep (France). This system comprises two six-column simulated mobile bed systems placed in series. In each simulated mobile bed system, the six columns have a diameter of 2.6 cm and a length of 10 cm, with the exception of one of them which has a length of 8 cm. The eluent used is ethanol and the chiral stationary phase is the Chiralpak AD phase available from Daicel Chemical Industries.

For the first step (first simulated mobile bed), zones I and IV contain one column and zones II and III contain two columns. The total concentration of the charge is 132.9 g/l, the period is 0.98 min and the pressure is 40 bar. The flow rates are 55.0 ml/min for zone I, 1.6 ml/min for the charge; 10.3 ml/min for the eluent; 9.0 ml/min for the extract and 2.9 ml/min for the raffinate.

For the second step (second simulated mobile bed), zones I and IV contain one column and zones II and III contain two columns. The total concentration of the charge is 102 g/l, the period is 0.98 min and the pressure is 40 bar. The flow rates are 55.0 ml/min for zone I; 1.1 ml/min for the charge; 11.1 ml/min for the eluent; 8.6 ml/min for the extract and 3.6 ml/min for the raffinate.

The yields and purities obtained for each enantiomer of α-ethyl-2-oxo-1-pyrrolidineacetamide at the end of step 1 and of step 2 are summarized in Table 1.

TABLE 1

|  | Extract | Raffinate |
|---|---|---|
| Step 1 |  |  |
| Conc. S enantiomer (g/l) | 11.5 | 1.5 |
| Conc. R enantiomer (g/l) | 2.0 | 35.1 |
| Purity (%) | 85 | 96 |
| Step 2 |  |  |
| Conc. S enantiomer (g/l) | 10.8 | 1.2 |
| Conc. R enantiomer (g/l) | 0.24 | 3.8 |
| Purity (%) | 97.8 | 76.0 |

This example shows that after the first step, the S enantiomer is obtained in an intermediate purity and a high level of recovery, and the R enantiomer is obtained in high purity. The S enantiomer of intermediate purity is then purified to 98% by passage through the second simulated mobile bed system, with an overall level of recovery of greater than 90%.

By varying the experimental parameters slightly (immobilization on a support, consumption of eluent), levels of recovery of the S enantiomer of about 97% can even be achieved.

EXAMPLE 2

Production Efficiency on the Pilot Industrial Scale

The Licosep 6-200 simulated mobile bed system, available from Novasep (France) is used, containing six columns having a diameter of 20 cm and a height of 10 cm, except for one of them which has a height of 8 cm. The stationary phase used is Chiralpak AD, available from Daicel Chemical Industries. The eluent used is a 40/60 (v/v) heptane/ethanol mixture. The raffinate and the eluent leave the simulated mobile bed, having been diluted (6 g/l and 3 g/l respectively), and are preconcentrated on falling-film evaporators. The distilled solvents are recycled.

The concentration of charge is 40 g/l; the period is 1.74 min and the pressure of the system is between 32 and 45 bar. This system is equipped with a device for recycling the eluent.

Different batches of racemic mixture of α-ethyl-2-oxo-1-pyrrolidineacetamide were separated in this system, using the following operating conditions

| charge flow rate (l/h) | 10.9 |
|---|---|
| eluent flow rate (l/h) | 95.1 |
| extract flow rate (l/h) | 69 |
| raffinate flow rate (l/h) | 37 |
| recycling flow rate (l/h) | 182.3 |

These operating conditions make it possible to collect the (S) enantiomer of the α-ethyl-2-oxo-1-pyrrolidineacetamide (extract) in an optical purity of greater than or equal to 98% and the (R) enantiomer of the α-ethyl-2-oxo-1-pyrrolidineacetamide (raffinate) in an optical purity of considerably greater than 85%.

The material balance by mass for this pilot study is very satisfactory: for 636.1 kg of racemic mixture consumed, 305.4 kg of S enantiomer and 299.9 kg of R enantiomer are recovered. The production efficiency with respect to (S)-α-ethyl-2-oxo-1-pyrrolidineacetamide in this system is 500 g/kg of chiral stationary phase/day.

EXAMPLE 3

Industrial-Scale Production Efficiency

In this example, the Licosep 6-450 simulated mobile bed system is used (available from Novasep, France), containing 6 columns having an inside diameter of 45 cm and a height of 8.5 cm. The stationary phase used is the Chiralpak AD stationary phase (available from Daicel Chemical Industries).

The eluent used is a 40/60 (v/v) heptane/ethanol mixture. The charge concentration is 40 g/l; the period is 1.06 min and the pressure of the system is between 24 and 36 bar. The extract and the raffinate leave the simulated mobile bed at respective concentrations of about 3 and 6 g/l. They are preconcentrated by continuous evaporation to about 100 g/l; the solvents distilled off are recycled.

Different batches of racemic mixture of α-ethyl-2-oxo-1-pyrrolidineacetamide were separated in this system, using the following operating conditions:

| charge flow rate (l/h) | 95 |
|---|---|
| eluent flow rate (l/h) | 715 |
| extract flow rate (l/h) | 480 |
| raffinate flow rate (l/h) | 330 |
| recycling flow rate (l/h) | 1480 |

These operating conditions make it possible to collect the (S) enantiomer of α-ethyl-2-oxo-1-pyrrolidineacetamide (extract) in an optical purity of greater than or equal to 98% and the (R) enantiomer of α-ethyl-2-oxo-1-pyrrolidineacetamide (raffinate) in an optical purity of greater than 95%.

The recovery yield is about 97%. The production efficiency with respect to (S)-α-ethyl-2-oxo-1-pyrrolidineacetamide in this system is 900 g/kg chiral stationary phase/day.

What is claimed is:

1. A process for separating (S)-α-ethyl-2-oxo-1-pyrrolidineacetamide and (R)-α-ethyl-2-oxo-1-pyrrolidineacetamide corresponding to the formulae

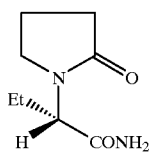

(I(S))

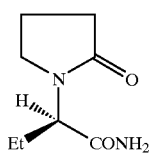

(I(R))

from a racemic mixture of α-ethyl-2-oxo-1-pyrrolidineacetamide, which comprises passing the racemic mixture of α-ethyl-2-oxo-1-pyrrolidineacetamide through a simulated mobile bed chromatography system, comprising at least three columns filled with chiral stationary phase.

2. The process according to claim 1, wherein the chiral stationary phase is selected from phases based on silica gel supporting polymeric compounds.

3. The process according to claim 2, wherein the chiral stationary phase is selected from phases based on silica gel supporting polysaccharide derivatives, polyacrylic derivatives or polyamide derivatives.

4. The process according to claim 2, wherein the chiral stationary phase is a phase based on silica gel supporting an ester or a carbamate of cellulose or of amylose.

5. The process according to claim 1, wherein the columns are less than or equal to 10 cm in height.

6. The process according to claim 1, wherein the simulated mobile bed system comprises 6 columns.

7. The process according to claim 1, wherein the racemic mixture is passed through two simulated mobile bed systems comprising 6 columns, the two simulated mobile bed systems being placed in series.

8. The process according to claim 7, wherein a step of evaporation is conducted between the two simulated mobile bed systems.

9. The process according to claim 1, wherein the simulated mobile bed system uses an eluent selected from ethanol or a mixture of heptane and ethanol.

10. The process according to claim 9, wherein the eluent is recycled.

* * * * *